US007655019B2

(12) United States Patent
LeVaughn et al.

(10) Patent No.: US 7,655,019 B2
(45) Date of Patent: Feb. 2, 2010

(54) BLOOD SAMPLING DEVICE

(75) Inventors: Richard W. LeVaughn, Newnan, GA (US); Gwenn E. Kennedy, Ellenwood, GA (US); Stephen J. Flynn, Peachtree City, GA (US); Carl E. Griffin, Marietta, GA (US); John C. Irwin, Woodstock, GA (US); Mary Kate Pynes, Dallas, GA (US); Stephanie J. Campbell, Kennesaw, GA (US); Christopher J. Ruf, Marietta, GA (US); Mitchell A. Solis, Cumming, GA (US); Avi M. Robbins, Longwood, FL (US); Jason R. Heath, Marietta, GA (US)

(73) Assignee: Facet Technologies, LLC, Kennesaw, GA (US)

( * ) Notice: Subject to any disclaimer, the term of this patent is extended or adjusted under 35 U.S.C. 154(b) by 644 days.

(21) Appl. No.: 10/569,025

(22) PCT Filed: Aug. 19, 2004

(86) PCT No.: PCT/US2004/026760

§ 371 (c)(1),
(2), (4) Date: Feb. 17, 2006

(87) PCT Pub. No.: WO2005/018425

PCT Pub. Date: Mar. 3, 2005

(65) Prior Publication Data

US 2006/0235454 A1    Oct. 19, 2006

Related U.S. Application Data

(60) Provisional application No. 60/497,046, filed on Aug. 20, 2003.

(51) Int. Cl.
A61B 17/14    (2006.01)
A61B 17/32    (2006.01)
(52) U.S. Cl. ...................................................... 606/183
(58) Field of Classification Search ................. 606/167, 606/181, 182, 183; 604/22, 117, 110, 207–211
See application file for complete search history.

(56) References Cited

U.S. PATENT DOCUMENTS 4,627,445 A    12/1986    Garcia et al.

(Continued)

FOREIGN PATENT DOCUMENTS

DE    19819407    11/1999

(Continued)

*Primary Examiner*—Todd E Manahan
*Assistant Examiner*—Michael G Mendoza
(74) *Attorney, Agent, or Firm*—Gardner Groff Greenwald & Villanueva, PC

(57) ABSTRACT

A sampling device (20) having a housing (24) with a lancet cartridge (22) mounted therein. The lancets (26) of the lancet cartridge (22) are interconnected by a flexible web (28). The lancet cartridge (22) is not positively engaged within the housing (24) and can be easily removed. The housing (24) has an opening (42) with an adjacent flexible or compressible fin (60) for dampening the motion of the lancet (26). The lancet cartridge (22) has at least one lancet (26) with an endcap, and the housing has a cap-removal mechanism (74) for separating the endcap from the housing (24). Anti-tampering features prevent opening of the device when the lancet cartridge (22) is oriented with a lancet (26) in a firing position.

20 Claims, 7 Drawing Sheets

U.S. PATENT DOCUMENTS

| | | | |
|---|---|---|---|
| 4,787,398 A | 11/1988 | Garcia et al. | |
| 4,794,926 A | 1/1989 | Munsch et al. | |
| 4,823,806 A | 4/1989 | Bajada | |
| 4,869,249 A | 9/1989 | Crossman et al. | |
| 4,990,154 A * | 2/1991 | Brown et al. | 606/182 |
| 5,035,704 A | 7/1991 | Lambert et al. | |
| 5,279,294 A | 1/1994 | Anderson et al. | |
| 5,318,584 A | 6/1994 | Lange et al. | |
| 5,514,152 A | 5/1996 | Smith | |
| 5,628,765 A | 5/1997 | Morita | |
| 5,741,288 A | 4/1998 | Rife | |
| 5,797,940 A | 8/1998 | Mawhirt et al. | |
| 5,871,494 A | 2/1999 | Simons et al. | |
| 5,951,492 A | 9/1999 | Douglas et al. | |
| 5,971,941 A | 10/1999 | Simons et al. | |
| 6,036,924 A | 3/2000 | Simons et al. | |
| 6,071,294 A | 6/2000 | Simons et al. | |
| 6,099,484 A | 8/2000 | Douglas et al. | |
| 6,156,050 A | 12/2000 | Davis et al. | |
| 6,228,100 B1 | 5/2001 | Schraga | |
| 6,472,220 B1 | 10/2002 | Simons et al. | |
| 6,530,892 B1 | 3/2003 | Kelly | |
| 6,766,817 B2 | 7/2004 | da Silva | |
| 2003/0199789 A1 | 10/2003 | Boecker et al. | |
| 2003/0199790 A1 | 10/2003 | Boecker et al. | |
| 2003/0199791 A1 | 10/2003 | Boecker et al. | |
| 2003/0199893 A1 | 10/2003 | Boecker et al. | |
| 2003/0199894 A1 | 10/2003 | Boecker et al. | |
| 2003/0199895 A1 | 10/2003 | Boecker et al. | |
| 2003/0199896 A1 | 10/2003 | Boecker et al. | |
| 2003/0199897 A1 | 10/2003 | Boecker et al. | |
| 2003/0199898 A1 | 10/2003 | Boecker et al. | |
| 2003/0199899 A1 | 10/2003 | Boecker et al. | |
| 2003/0199900 A1 | 10/2003 | Boecker et al. | |
| 2003/0199901 A1 | 10/2003 | Boecker et al. | |
| 2003/0199902 A1 | 10/2003 | Boecker et al. | |
| 2003/0199903 A1 | 10/2003 | Boecker et al. | |
| 2003/0199904 A1 | 10/2003 | Boecker et al. | |
| 2003/0199905 A1 | 10/2003 | Boecker et al. | |
| 2003/0199906 A1 | 10/2003 | Boecker et al. | |
| 2003/0199907 A1 | 10/2003 | Boecker et al. | |
| 2003/0199908 A1 | 10/2003 | Boecker et al. | |
| 2003/0199909 A1 | 10/2003 | Boecker et al. | |
| 2003/0199910 A1 | 10/2003 | Boecker et al. | |
| 2003/0199911 A1 | 10/2003 | Boecker et al. | |
| 2003/0212424 A1 | 11/2003 | Briggs et al. | |
| 2004/0009100 A1 | 1/2004 | Simons et al. | |
| 2004/0010279 A1 | 1/2004 | Freeman et al. | |
| 2004/0049220 A1 | 3/2004 | Boecker et al. | |
| 2004/0087990 A1 | 5/2004 | Boecker et al. | |
| 2004/0092944 A1 | 5/2004 | Penenberg | |
| 2004/0092995 A1 | 5/2004 | Boecker et al. | |
| 2004/0098009 A1 | 5/2004 | Boecker et al. | |
| 2004/0102803 A1 | 5/2004 | Boecker et al. | |

FOREIGN PATENT DOCUMENTS

| | | |
|---|---|---|
| DE | 10057832 | 2/2002 |
| DE | 20213607.8 | 7/2003 |
| DE | 10208575.7 | 8/2003 |
| DE | 10245721 | 12/2003 |
| EP | 0449525 | 10/1991 |
| EP | 0811843 | 12/1997 |
| EP | 0877250 | 11/1998 |
| EP | 0949506 | 10/1999 |
| EP | 0589186 | 11/1999 |
| EP | 0985376 | 3/2000 |
| WO | WO 01/66010 | 9/2001 |
| WO | WO 02/36010 | 5/2002 |
| WO | WO 03/070099 | 8/2003 |
| WO | WO 03/071940 | 9/2003 |
| WO | WO 03/088835 | 10/2003 |

* cited by examiner

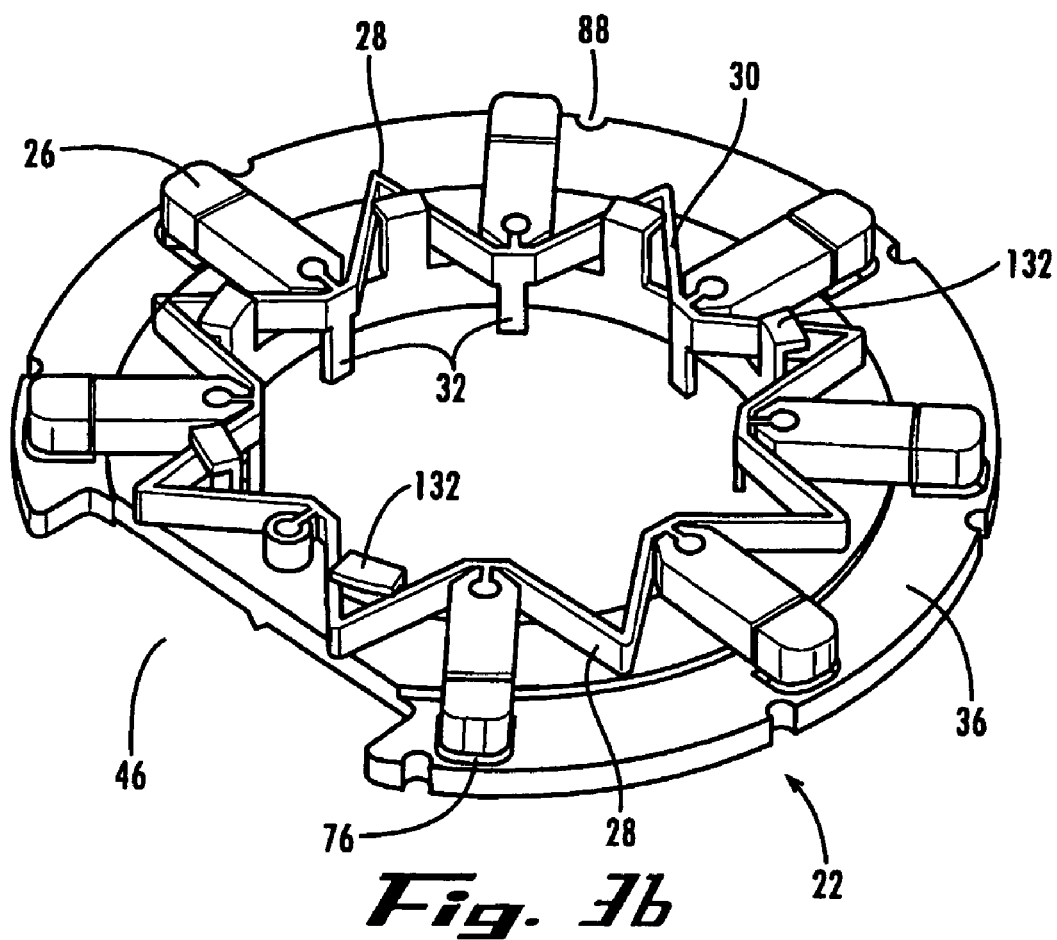

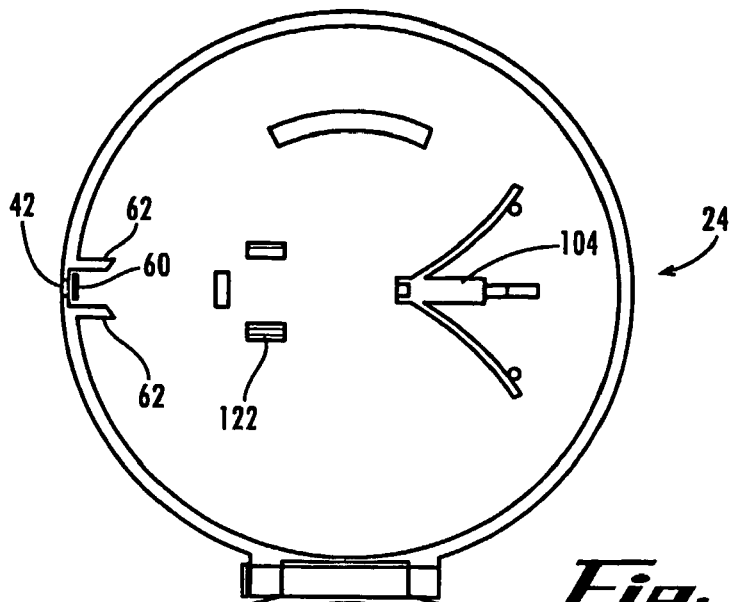
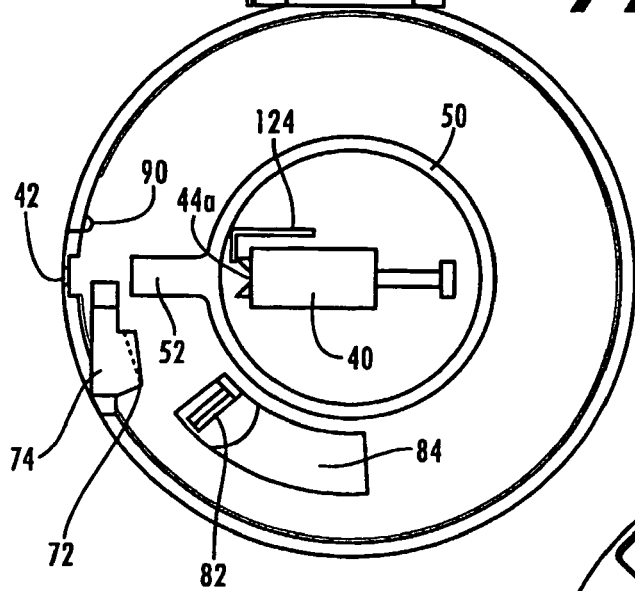
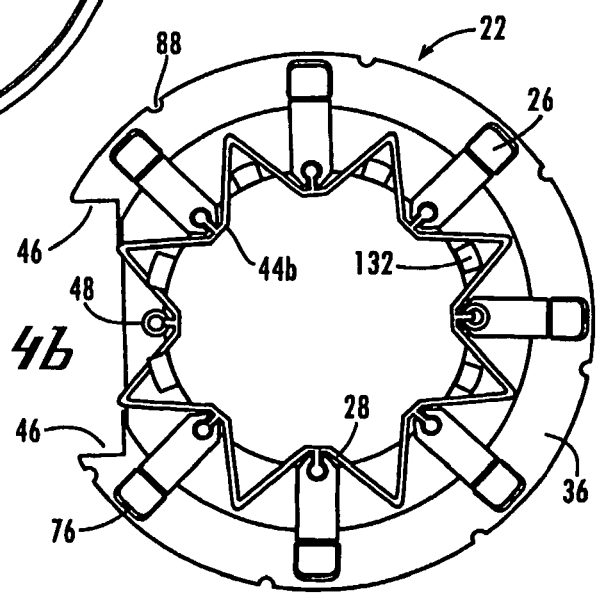
Fig. 4a
Fig. 4b

BLOOD SAMPLING DEVICE

CROSS-REFERENCE TO RELATED APPLICATIONS

This application claims the benefit of U.S. Provisional Patent Application Ser. No. 60/497,046, filed Aug. 20, 2003, the entire content of which is hereby incorporated herein by reference for all purposes.

TECHNICAL FIELD

The present invention relates generally to medical devices and procedures, and more particularly to lancing devices for the collection and/or analysis of samples of blood or other bodily fluid.

BACKGROUND OF THE INVENTION

Many medical procedures require puncturing of the skin, and sometimes underlying tissues, of an animal or human subject. For example, a sharp lancet tip is commonly used to puncture the subject's skin at a lancing site to obtain a sample of blood, interstitial fluid or other body fluid, as for example in blood glucose monitoring by diabetics, and in blood typing and screening applications. In some instances, a person must periodically sample their blood for multiple testing throughout the day or week. Because re-use of a lancet can result in infection or spread of bloodborne contaminants, persons requiring repeated testing often must carry multiple lancets with them. This can be inconvenient and lead to reduced compliance with a prescribed test regimen. Accordingly, it can be seen that needs exist for a convenient, compact multi-use lancing device.

Various devices are known for sampling blood and other body fluids for analysis of the condition of a human or other animal subject. For example, U.S. Pat. No. 5,971,941 is understood to show a cassette with test strips for placement by a slider. A lancet pierces the skin surface so that blood can be obtained for analysis. The lancets are integrated on a test strip, and are positioned together with the test strip. Another embodiment is understood to show a disposable cylindrical insert having a lancet and a test membrane with an aperture for the lancet. The insert is inserted in a mounting cavity of a plunger or piston, which forces the lancet outward for blood withdrawal. DE 198 19 407 A1 is understood to show a multiplicity of test strips with integrated lancets for insertion into an analysis device.

U.S. Pat. No. 4,787,398 is understood to show a device with a plunger for directing a lancet outward, and has an evaluation system and a display system. A replaceable unit is applied to the device for each measurement. The replaceable unit comprises the lancet and a test strip, which is wetted with blood. This replaceable unit is thrown away after each use. EP 0 449 525 A1 is understood to show a blood withdrawal system wherein a new lancet is inserted manually into a release device before each use. A test strip is then inserted into the device. U.S. Pat. No. 4,627,445 is understood to show a device for measuring blood sugar, with an integrated blood withdrawal unit. A new replaceable lancet and test elements must be installed to the device for testing, and afterward disassembled. U.S. Pat. No. 5,951,492 is understood to show a disposable unit with a capillary tube and a test strip, to which sampled blood taken is applied. The capillary tube includes a lancet. A new disposable unit is attached and removed before and after each measurement.

EP 0877250 A2, EP 0949506 A2 and EP 811843 A2 are understood to show devices having a multiplicity of test elements arranged on a rotatable disk carrier. The test elements are brought successively into a working position and pushed out of the housing to be wetted with blood. U.S. Pat. No. 6,228,100 and U.S. Pat. No. 4,794,926 are understood to show lancets arranged on a carrier, which is rotated with respect to a housing.

German Application DE 100 57 832 C1 is understood to show a lancing device of a known form. Other lancing devices understood to include multiple lancets are shown, for example, in U.S. Pat. No. 6,540,675 and WO 02/36010 A1. EP 0589186 B1 is understood to show a lancet with a removable protective cap. WO 01/66010 A1 is understood to include a multiplicity of lancets in a magazine, with an opening of the chamber closed by an elastic material, which is penetrated in the puncture process.

Known sampling devices have, however, not proven fully satisfactory to all users for a variety of reasons. Accordingly, it is to the provision of an improved sampling device that the present invention is primarily directed.

SUMMARY OF THE INVENTION

Briefly described, example embodiments of the present invention include an improved sampling device that is convenient, compact, and includes multiple lancets in a single cassette or cartridge. The present invention preferably increases convenience for the user, thereby encouraging more frequent testing and insuring compliance with the subject's prescribed testing regimen.

In one aspect, the invention is a device for sampling a body fluid. The device preferably includes a housing and a lancet cartridge removably installed within the housing. The device preferably also includes a drive mechanism within the housing for propelling an active lancet from a retracted position fully within the lancet cartridge to an extended position wherein at least a tip portion of the lancet projects outward from the lancet cartridge. The drive mechanism preferably includes a contact face for imparting motion to the active lancet without positive attachment to the lancet cartridge.

In another aspect, the invention is a device for sampling a body fluid. The device preferably includes a housing having an opening therein, a lancet, and a drive mechanism within the housing for propelling the lancet along a lancing path from a retracted position fully within the lancet cartridge to an extended position wherein at least a tip portion of the lancet projects through the opening in the housing. The device preferably also includes a dampening fin adjacent the opening for dampening the motion of the lancet upon contact of the lancet against the dampening fin in the extended position.

In another aspect, the invention is a device for sampling a body fluid. The device preferably includes a housing and a lancet cartridge removably installed within the housing. The housing preferably includes an internal shelf, and the lancet cartridge includes at least one hook. The at least one hook engage(s) the internal shelf of the housing to prevent opening of the housing when the lancet cartridge is in a first position, and release(s) the internal shelf of the housing to permit opening of the housing when the lancet cartridge is in a second position.

In still another aspect, the invention is a device for sampling a body fluid, the device including a housing and a plurality of lancets contained within said housing. The plurality of lancets are preferably interconnected by a flexible web.

In another aspect, the invention is a device for sampling a body fluid, the device preferably including a housing having an arm with a wedge-shaped profile; at least one lancet, each lancet having a body portion, a sharp tip extending from the body portion, and an endcap covering the sharp tip; and an advancing mechanism for advancing the at least one lancet into contact with the arm of the housing to drive the wedge-shaped profile between the body portion of the lancet and the endcap, and thereby separate the endcap from the body portion of the lancet.

In another aspect, the invention is a lancet cassette for removable installation within a sampling device, the lancet cassette preferably including a plurality of lancets and a flexible web interconnecting the plurality of lancets.

In yet aspect, the invention is a device for sampling a body fluid. The device preferably includes an outer housing having first and second portions hingedly connected to one another, an opening, and an arm having a wedge-shaped profile projecting inwardly from one of the first and second portions. The device preferably also includes a lancet cassette for removable installation within the outer housing, the lancet cassette comprising a plurality of lancets arranged in a circular array, and a flexible web interconnecting the plurality of lancets, each lancet comprising a lancet body, a sharp tip, and a protective endcap removably positioned over the sharp tip. The device preferably also includes a drive mechanism within the housing for propelling an active lancet along a lancing path, from a retracted position fully within the lancet cartridge to an extended position wherein at least a tip portion of the active lancet projects through the opening in the housing. And the device preferably includes an advancing mechanism for sequentially advancing each of the plurality of lancets into an active position in the housing, wherein the endcap of the active lancet is separated from the body portion thereof as it enters the active position by contact with the wedge-shaped profile.

These and other aspects, features and advantages of the invention will be understood with reference to the drawing figures and detailed description herein, and will be realized by means of the various elements and combinations particularly pointed out in the appended claims. It is to be understood that both the foregoing general description and the following brief description of the drawings and detailed description of the invention are exemplary and explanatory of preferred embodiments of the invention, and are not restrictive of the invention, as claimed.

BRIEF DESCRIPTION OF THE DRAWINGS

FIGS. 3a and 3b show perspective views of the sampling device of FIG. 3 with its cartridge removed from its outer housing.

FIGS. 4a and 4b show a top view of the sampling device of FIG. 3 with the cartridge removed from the outer housing.

DETAILED DESCRIPTION OF EXAMPLE EMBODIMENTS

Figure 1A:
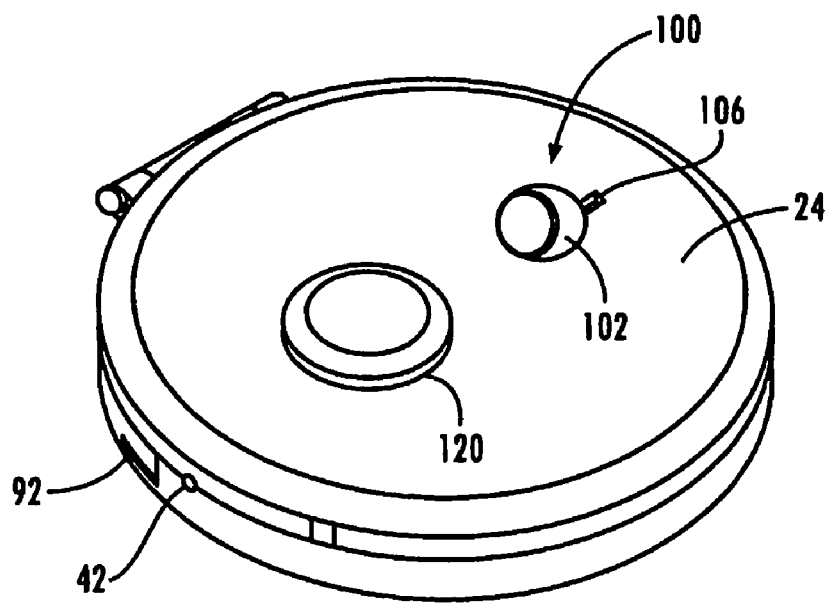
FIGS. 1a-1d are top and bottom perspective views, a top view, and a side view, respectively, of a sampling device according to an example embodiment of the present invention.
Figure 1B:
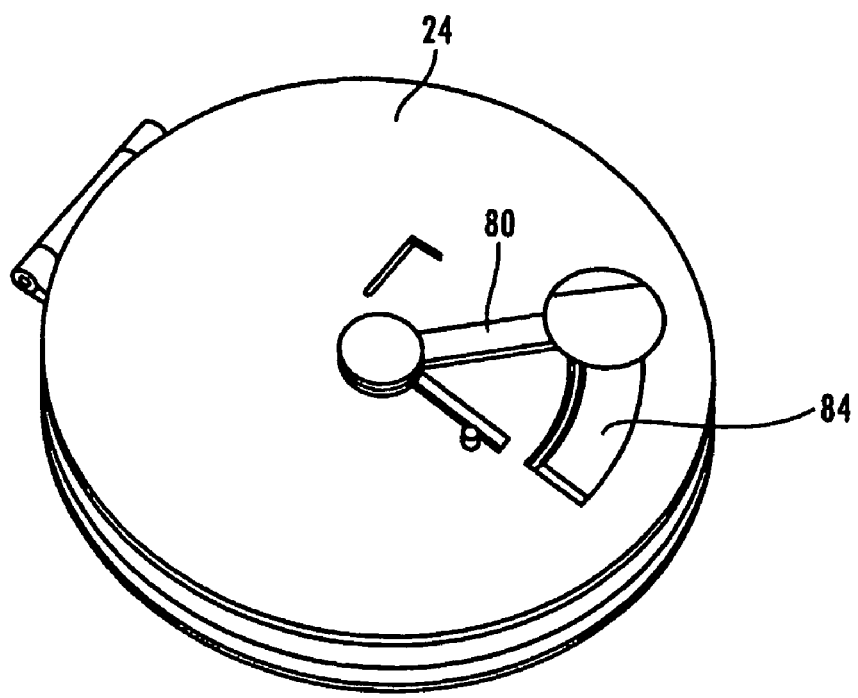
Figure 1C:
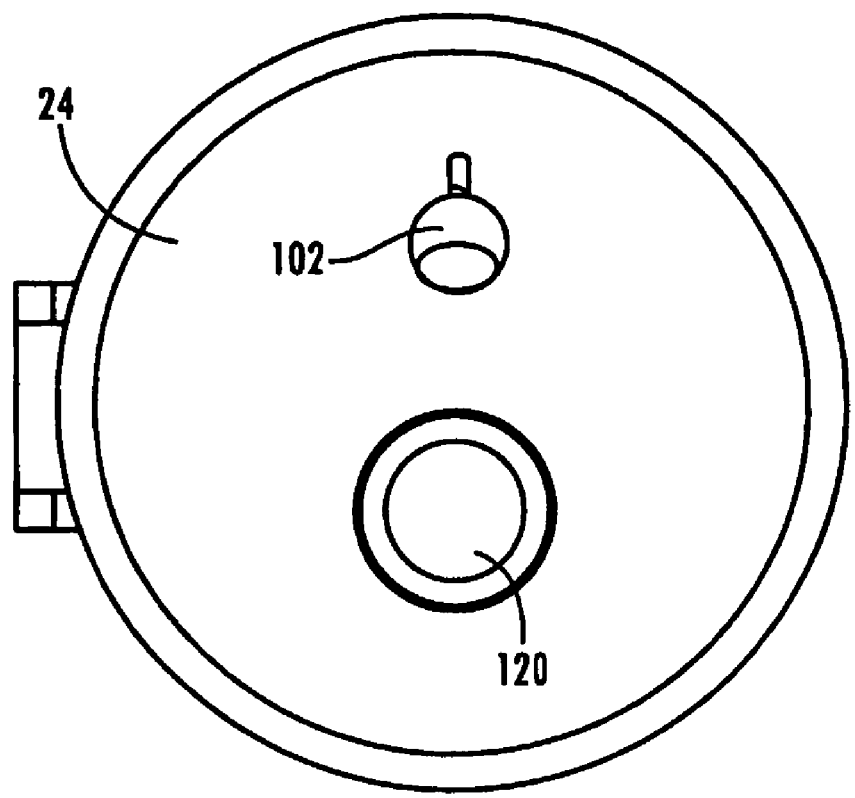
Figure 1D:
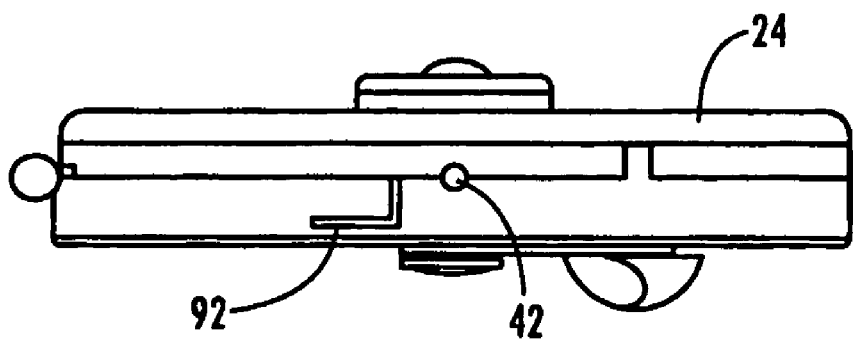
Figure 2:
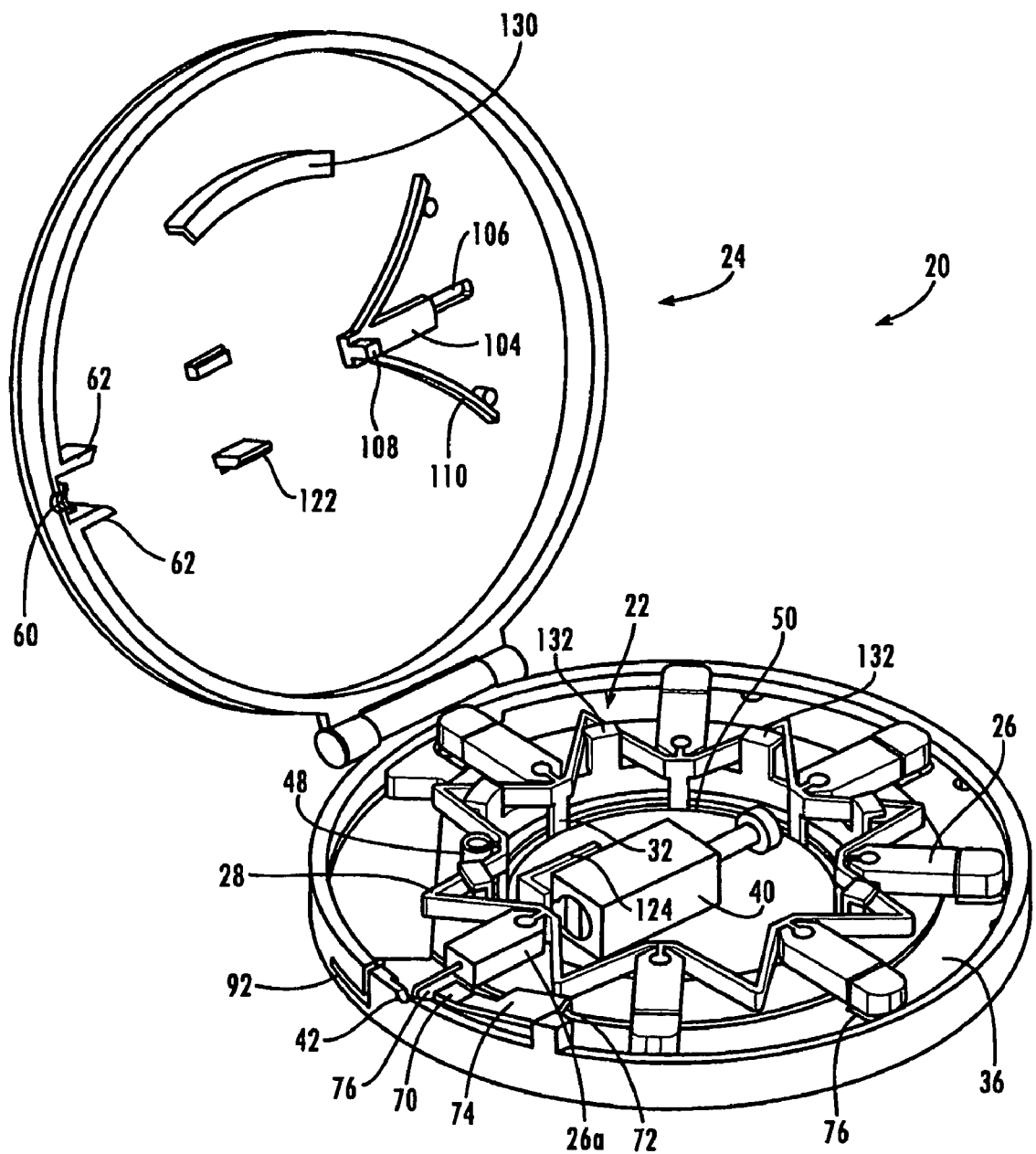
FIG. 2 is a perspective view of a sampling device according to an example embodiment of the present invention, shown with its outer housing open.

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

In an example embodiment, the present invention is a sampling device 20 comprising a replaceable cartridge 22 and a re-usable outer housing 24. The cartridge 22 preferably comprises a plurality of lancets 26, each lancet preferably having a lancet body, a needle or blade with a sharp tip extending from the body, and an endcap covering the sharp tip. The lancets 26 are preferably interconnected by a flexible web 28. The web 28 may be integrally formed with the lancets 26, or the lancets can be attached to the web, as for example by a key-and-slot coupling, adhesive, thermal or solvent welding, mechanical connectors, or the like. In the depicted embodiment, the lancets 26 are oriented generally radially in a generally circular ring, and lying within a plane, with their sharp tips directed radially outwardly. In other embodiments, the lancets are arranged in a linear array or otherwise interconnected.

The web 28 preferably comprises a zig-zagged array of interconnected legs 30 angularly connected to one another. For example, in the depicted circular array of lancets 26, the web 28 comprises a generally star-shaped array of legs 30 (seen best in the top view of FIG. 4b), with adjacent legs connecting to one another along an inner ring and an outer ring in alternating sequence, and with the base of each lancet connected to the web at a connection point along the inner ring. The web 28 preferably further comprises alignment tabs 32 projecting through a central opening of the cartridge generally perpendicular to the plane of the lancets. The web 28 is preferably formed of a flexible resilient polymeric or rubber material, allowing the lancets to move independently of one another when fired, but having sufficient shape memory to impart an inward biasing force on the active lancet after firing to serve as a retraction spring for returning the lancet from an extended lancing position, wherein the sharp lancet tip extends out of the housing, to a retracted position fully within the housing, thereby preventing accidental needle sticks and/or contamination. The lancets and web are preferably mounted to a cartridge base or carrier 36. In the depicted example, the cartridge base is an annular disk having an outer circumferential edge or rim, and a central opening forming an inner circumferential edge or rim.

The housing 24 preferably comprises a generally hollow shell having first and second half-shells hingedly connected to one another in clamshell fashion. In the depicted embodiment, the housing 24 is generally disk-shaped with a circular profile. A drive mechanism 40 is preferably mounted within the housing for driving the lancets along a lancing stroke between a retracted position within the housing and an extended position wherein at least the sharp tip of the lancet extends outwardly of the housing, through an opening 42, to penetrate the skin of a human or animal subject at a sampling site. The drive mechanism preferably comprises a spring, cam, motor or other driving means for imparting force upon an active one of the lancets 26 upon firing. In a preferred form, seen best with reference to FIG. 4a, the piston or hammer of the drive mechanism 40 and the lancet cartridge 22 have self-aligning surface profiles on their respective contact faces. For example, in the depicted embodiment, the drive piston comprises an angled female recess 44a, and the lancet cartridge has a complementary angled male profile 44b at the base of each lancet 26, which is adapted to cooperatively align with and contact the drive piston when the device is fired. In alternate embodiments, the contact faces are flat or otherwise configured, and alternate means of alignment are provided.

The drive mechanism 40 directly or indirectly impacts the base of each lancet 26 upon firing, but preferably does not positively engage the lancet or any other portion of the lancet cartridge 22. In this manner, a spent lancet cartridge is more easily removed and replaced, as there is no need to align or engage the cartridge with the drive mechanism for removal or insertion. This also allows the lancet cartridge 22 to be advanced to move sequential lancets 26 on the cartridge into the active or firing position, regardless of the position or state (e.g., cocked or uncocked) of the drive mechanism 40. And because the active lancet 26a is not coupled to the drive mechanism as the drive mechanism is cocked, the lancets 26 can be initially mounted on the lancet cartridge 22 in a ready-to-fire configuration, and the lancets themselves need not be moved through a cocking sequence prior to firing. The cartridge 22 preferably further comprises a recessed segment 46 formed by a cutout section of the cartridge base, for clearance and alignment during insertion and removal of a cartridge to and from the housing. Preferably, no lancet is attached to the web 28 adjacent the recessed segment, and the cartridge base preferably comprises an attachment lug 48 adjacent the recessed segment having a slot for connection with a cooperating key or projection on the web.

A generally circular ring-shaped groove or channel 50 is preferably provided in an inner face of the housing 24, forming a track in which the alignment tabs 32 of the lancet cartridge ride as the cartridge is rotationally advanced within the housing for sequential firing of its lancets 26, to provide alignment of the cartridge in the housing and to prevent snagging of the lancets with the housing as the cartridge is advanced. A radial extension groove or channel 52 extends outwardly from the circular groove 50 toward the opening 42 in the housing 24 at the firing position, to provide clearance for the alignment tab 32 of the active lancet 26a as it is driven along the advancing portion of its lancing stroke from its retracted position to its extended position upon firing, and as it is withdrawn back from the extended position to the retracted position on the return portion of the lancing stroke after firing.

The housing 24 preferably also includes a flexible or compressible dampening fin 60 positioned adjacent and radially inwardly of the opening 42 of the housing. As the active lancet 26a advances into its extended position upon firing, a forward face of the lancet body contacts the fin 60 to dampen the impact of the lancet against the housing. By reducing the noise and vibration sensed by the user upon lancing, the perceived pain and resultant anxiety may be reduced. The fin 60 may also serve to control the speed of the lancet as it penetrates the skin, further reducing pain and anxiety of the user and possibly increasing compliance with a prescribed test regimen. The fin 60 may also serve to limit the travel of the lancet and thereby provide lancing depth control, and the radial position of the fin 60 on the housing is optionally adjustable to provide user-adjustable depth control.

The housing 24 preferably also includes one or more guide members for directing the path of the active lancet along its lancing stroke. In the depicted example embodiment, a pair of flanges 62 extend from an inner surface of the housing, adjacent to the opening 42 and extending radially inwardly. As the active lancet 26a advances into its extended position upon firing, the lancet is directed between inwardly inclined faces of the flanges 62 to closely control the path of the lancet to minimize or prevent any lateral or pivotal movement of the lancet as its sharp tip pierces the skin at the lancing site, thereby reducing tearing of the tissue and resultant pain.

Figure 3A:
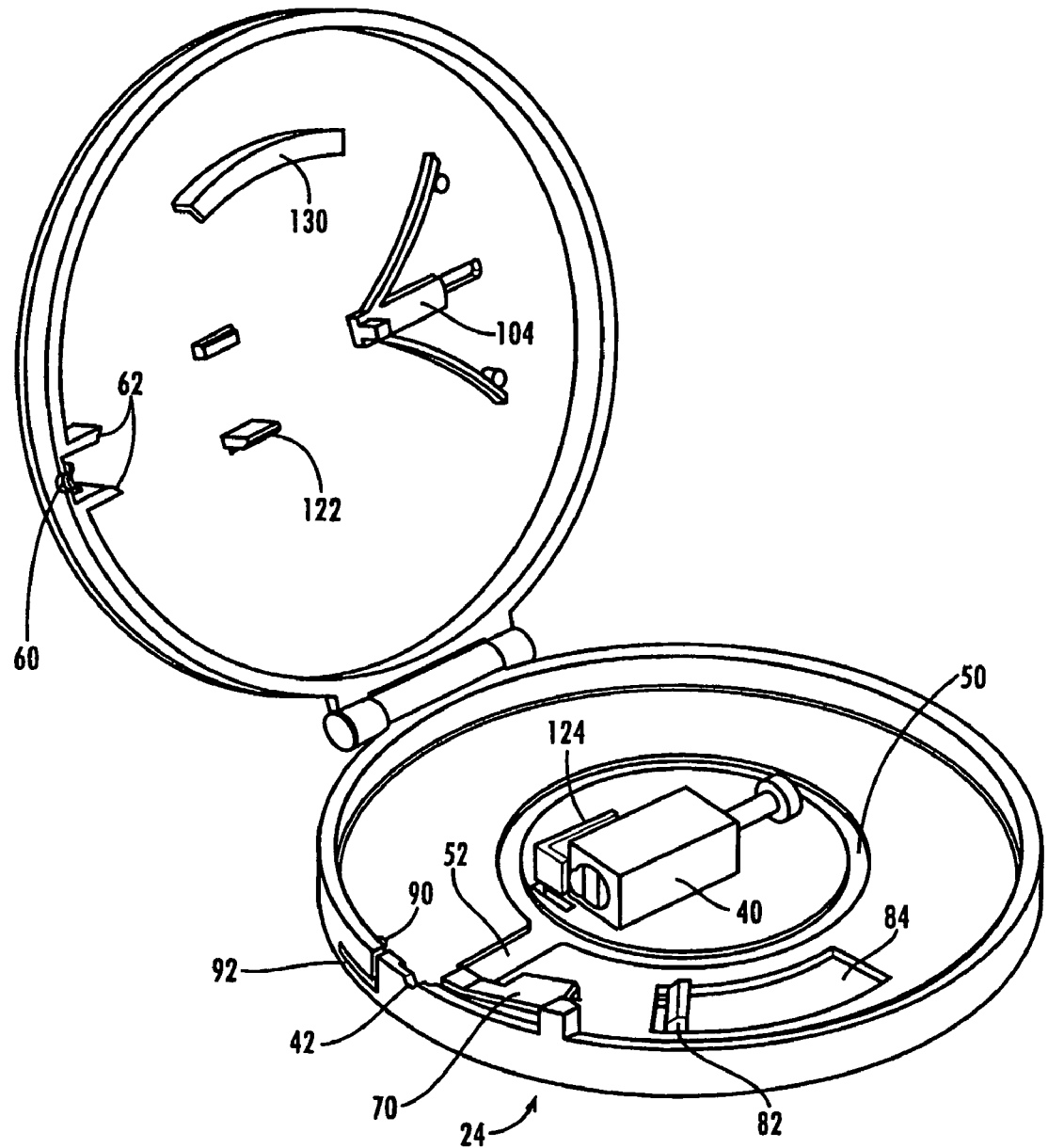
Figure 5A:
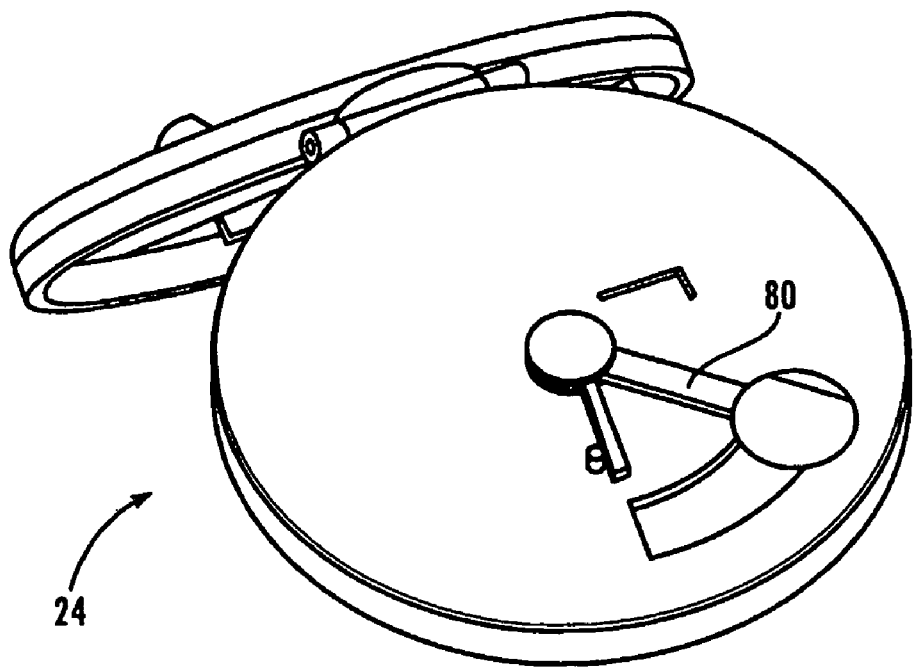
FIGS. 5a and 5b show a bottom view of the sampling device of FIG. 3 with the cartridge removed from the outer housing.
Figure 5B:
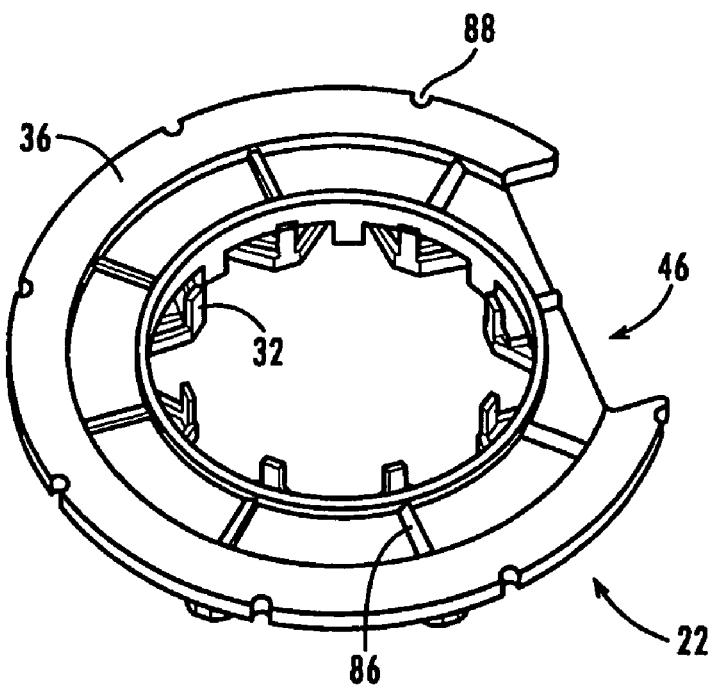

The housing 24 preferably also includes a cap removal mechanism for removing the endcap of each lancet as it is advanced into the firing position. In the depicted example, an arm 70 cantilevered from an inside surface of the housing 24 engages the endcap of each lancet 26 as it is advanced into the firing position to become the active lancet 26a, as shown in FIG. 3. A wedge 72 projects from the arm 70, and is positioned to align between the lancet body and the endcap. As the lancet cartridge 22 is advanced, the active lancet passes along the wedge, and its endcap engages an inclined face of the wedge to separate the endcap from the lancet body. A ramp portion 74 of the arm 70 engages the endcap and presses the endcap out of the firing plane of the lancets on the cartridge, and down into a well or recess 76 in the cartridge base 36, as the lancet cartridge is advanced to move the active lancet into the firing position. The endcaps and/or the well or recess 76 preferably comprise one or more crush pins, ribs or other projections or interengaging surface features to produce a press fit as each endcap is moved into its respective well or recess, thereby preventing rattling or jamming due to loose parts within the sampling device and ensuring that the severed endcaps are disposed with the rest of the lancet cartridge after all lancets are used.

The housing 24 preferably further comprises one or more mechanisms for advancing the lancet cartridge 22, cocking the drive mechanism 40, and triggering the drive mechanism to fire the active lancet. In the depicted example embodiment of the invention, separate mechanisms are provided for carrying out each of these actions in discrete steps. In alternate embodiments of the invention, combined mechanisms may be provided for carrying out any two or more of these actions together.

A cartridge-advancing arm 80 is preferably pivotally mounted to the lower half-shell of the housing 24, and includes a pawl 82 extending through an arcuate slot 84 into the housing. The pawl 82 engages ribs, recesses or other surface features 86 on the underside of the of the cartridge base 36, to rotationally advance the lancet cartridge 22 as the arm 80 is pivotally actuated by the user. One or more detents 88, protuberances 90 or other interengaging surface features are preferably provided on the cartridge 22 and/or the housing 24 to facilitate indexing and alignment of the cartridge with an active lancet in the firing position, and/or to provide tactile and/or audible feedback to the user to indicate the sequential advancement of the cartridge. An L-shaped slot 92 preferably forms a resilient cantilevered section of the housing 24 to bias a protuberance 90 or other surface feature on the housing into engagement with a cooperating detent 88 or other surface feature of the cartridge 22.

A cocking slide 100 is preferably mounted to the upper half-shell of the housing 24, with an outer knob 102 mounted outside the housing and connected to an inner member 104 inside the housing by a connecting strut extending through a radial slot 106 in the housing. The inner member 104 preferably comprises a finger 108 for engaging a cooperating portion of the drive mechanism 40 to cock the drive mechanism as the cocking slide is actuated by a user by linearly sliding the outer knob along the path defined by slot 106, for example by compressing a drive spring element of the drive mechanism. One or more spring arms 110 preferably extend between the inner member 104 and connecting pin(s) on the housing 24 to return the cocking slide to its ready position after cocking.

A trigger button 120 is preferably mounted to an exterior face of the upper half-shell of the housing 24, with an actuator 122 projecting through an opening through the housing shell into the housing's interior chamber. When the user depresses the trigger button 120, the actuator 122 contacts a cooperating latch 124 and draws the latch out of engagement with a cooperating portion of the drive mechanism to release the drive mechanism to impact the active lancet and drive it through its lancing stroke.

The device 20 preferably further comprises an anti-tamper mechanism to prevent the user from accessing the cartridge 22 inside the housing 24 until the cartridge is fully spent and all lancets 26 have been used. The anti-tamper mechanism enhances safety by reducing the likelihood of inadvertent opening of the housing and the resultant potential for contamination by contact with a used lancet, and by making it more difficult or inconvenient for the user to attempt to reuse lancets. A shelf 130 projects into the housing from an inner face of the upper half-shell, located for cooperative alignment with one or more hooks 132 projecting from the cartridge 22. When the cartridge is rotated into a loading/unloading position, with its recessed segment 46 oriented in the firing position between the drive mechanism 40 and the opening 42, all of the hooks 132 of the cartridge are out of alignment with the shelf 130, and the housing can be opened to access the cartridge for removal and replacement. But when the cartridge is rotated out of the loading/unloading position, with a lancet oriented in the firing position between the drive mechanism 40 and the opening 42, at least one of the hooks 132 of the cartridge is engaged between the shelf 130 and the inner face of the housing shell to prevent opening of the housing. In the depicted embodiment, the shelf 130 comprises an arcuate member having an upright panel projecting generally perpendicularly from the housing shell and a transverse portion extending from the upright panel generally parallel with the housing shell, and the hooks 132 move along an arcuate path concentric with the arcuate shelf as the cartridge is rotationally advanced. In this manner, the cartridge cannot be opened if any lancet is in the firing position, reducing the potential for injury or infectious contamination of the user and/or bystanders.

In use, the user loads a fresh lancet cartridge 22 into the housing by opening the housing and inserting the cartridge so that its recessed segment 46 is aligned in the firing position between the drive mechanism 40 and the opening 42. The housing is then closed. The cartridge is advanced by actuating the advance arm 80 to bring a first active lancet 26 into the firing position. Advancing a lancet into the firing position also locks the housing closed by engagement of the hooks 132 with the shelf 130. The drive mechanism is cocked or armed by actuating the cocking slide 100. The device is then positioned with the opening 42 against the subject's skin at the intended lancing site, and the trigger button is pressed to fire the device and drive the active lancet through its lancing stroke to pierce the skin at the lancing site and to return back to a retracted position within the housing under the influence of the flexible web 28. For subsequent lancing, the cartridge is sequentially advanced through the lancets on the cartridge, and the device is cocked and fired in like manner. When the cartridge is fully spent and all lancets have been used, the cartridge is advanced to bring the recessed segment 46 back into the firing position, thereby disengaging hooks 132 from shelf 130 and allowing the housing to be opened. Because the cartridge is preferably not positively engaged by the firing mechanism or the housing, it may easily be removed for replacement by simply tipping the housing over and allowing the cartridge to drop out.

While the invention has been described with reference to preferred and example embodiments, it will be understood by those skilled in the art that a variety of modifications, additions and deletions are within the scope of the invention, as defined by the following claims.

What is claimed is:

1. A device for sampling a body fluid, said device comprising a housing and a lancet cartridge removably installed within the housing, the lancet cartridge comprising a plurality of lancets arranged in a circular array and each having a sharp lancet tip directed radially outwardly, said lancets being interconnected to one another by a flexible web that allows the lancets to move independently of one another in a radial direction, the device further comprising a drive mechanism within the housing for propelling an active lancet selected from the plurality of lancets from a retracted position fully within the lancet cartridge radially outwardly to an extended position wherein at least a tip portion of the lancet projects outward from the lancet cartridge, said drive mechanism comprising a contact face for imparting motion to the active lancet without positive attachment to the lancet cartridge.

2. The sampling device of claim 1, wherein the contact face of the drive mechanism comprises an angled female recess, and the lancet cartridge has at least one complementary angled male profile for alignment within the angled female recess.

3. The sampling device of claim 1, wherein the housing comprises a resilient portion having a protuberance thereon for engaging at least one recess in the lancet cartridge to index advancement of the lancet cartridge within the housing.

4. A device for sampling a body fluid, said device comprising a housing having an opening therein, a plurality of lancets arranged in a circular array and each having a sharp lancet tip directed radially outwardly, said lancets being interconnected to one another by a flexible web that allows the lancets to move independently of one another in a radial direction, a drive mechanism within the housing for propelling the lancet along a lancing path, from a retracted position fully within the lancet cartridge to an extended position wherein at least a tip portion of the lancet projects through the opening in the housing, and a dampening fin adjacent the opening for dampening the motion of the lancet upon contact of the lancet against the dampening fin in the extended position.

5. The sampling device of claim 4, wherein the housing further comprises a pair of flanges positioned on opposite sides of the opening, said flanges having inwardly inclined faces for guiding the lancet along the lancing path.

6. A device for sampling a body fluid, said device comprising a housing and a plurality of lancets contained within said housing, said plurality of lancets being arranged in a circular array and each having a sharp lancet tip directed radially outwardly, said lancets being interconnected by a flexible web that allows the lancets to move independently of one another in a radial direction.

7. The sampling device of claim 6, further comprising a plurality of alignment tabs, each alignment tab associated with a respective one of the plurality of lancets, and wherein the housing comprises a channel in which the alignment tabs are received.

8. The sampling device of claim 7, wherein the channel comprises a ring-shaped channel portion and an extension channel portion extending radially from the ring-shaped channel portion.

9. A device for sampling a body fluid, said device comprising:
   a housing having an arm with a wedge-shaped profile and an inclined ramp;
   a plurality of lancets arranged in a co-planar array defining a firing plane, each lancet having a body portion, a sharp tip extending from the body portion, and an endcap covering the sharp tip;
   an advancing mechanism for advancing one of the plurality of lancets into contact with the arm of the housing to drive the wedge-shaped profile between the body portion of the lancet and the endcap, and thereby separate the endcap from the body portion of the lancet, and to drive the separated endcap into contact with the inclined ramp to move the separated endcap out of the firing plane; and
   the plurality of lancets being interconnected to one another by a flexible web that allows the lancets to move independently of one another in a radial direction.

10. The sampling device of claim 9, wherein the separated endcap is driven into a well for retaining the endcap out of the firing plane.

11. A lancet cassette for removable installation within a sampling device, said lancet cassette comprising a plurality of lancets arranged in a circular array and each having a sharp lancet tip directed radially outwardly, said lancets being interconnected to one another by a flexible web that allows the lancets to move independently of one another in a radial direction.

12. The lancet cassette of claim 11, further comprising a plurality of alignment tabs, each alignment tab attached to an inner end of a respective one of the plurality of lancets.

13. The lancet cassette of claim 12, wherein the plurality of lancets are positioned on an annular carrier disk having a central opening through which the plurality of alignment tabs project.

14. The lancet cassette of claim 11, further comprising at least one hook for engagement with an anti-tamper shelf portion of the sampling device.

15. The lancet cassette of claim 11, wherein each lancet comprises a removable protective endcap, and wherein the lancet cassette further comprises a well beneath the end cap of each lancet for retaining the endcap upon removal from the lancet.

16. The lancet cassette of claim 11, further comprising a lower face having surface features for engaging an advancing mechanism of the sampling device.

17. The lancet cassette of claim 11, further comprising an outer circumferential rim having a plurality of detents formed therein for indexing engagement with a cooperating protuberance of the sampling device.

18. A device for sampling a body fluid, said device comprising:
   an outer housing having first and second portions hingedly connected to one another, an opening, and an arm having a wedge-shaped profile projecting inwardly from one of the first and second portions;
   a lancet cassette for removable installation within the outer housing, the lancet cassette comprising a plurality of lancets arranged in a circular array within a firing plane, and a flexible web interconnecting the plurality of lancets that allows the lancets to move independently of one another in a radial direction and along the firing plane, each lancet comprising a lancet body, a sharp tip directed radially outwardly, and a protective endcap removably positioned over the sharp tip;
   a drive mechanism within the housing for propelling an active lancet along a lancing path in the firing plane, from a retracted position fully within the lancet cartridge radially outwardly to an extended position wherein at least a tip portion of the active lancet projects through the opening in the housing; and
   an advancing mechanism for sequentially advancing each of the plurality of lancets into an active position in the housing, wherein the endcap of the active lancet is separated from the body portion thereof as it enters the active position by contact with the wedge-shaped profile and wherein the separated endcap is moved out of the firing plane.

19. The sampling device of claim 18, further comprising a dampening fin adjacent the opening in the housing for contact with the active lancet in its extended position.

20. The sampling device of claim 18, further comprising a guide channel defined between a pair of flanges positioned on opposite sides of the opening through the outer housing.

* * * * *